United States Patent

Schönauer et al.

[11] Patent Number: 5,352,353
[45] Date of Patent: Oct. 4, 1994

[54] DEVICE FOR MONITORING THE CONCENTRATION OF GASEOUS CONSTITUENTS IN MIXTURES OF GASES

[75] Inventors: Ulrich Schönauer; Edelbert Häfele, both of Karlsruhe, Fed. Rep. of Germany

[73] Assignees: Roth-Technik GmbH & Co.; Forschung für Automobil- und Umelttechnik, both of Gaggenau, Fed. Rep. of Germany

[21] Appl. No.: 173,713

[22] Filed: Dec. 23, 1993

Related U.S. Application Data

[63] Continuation of Ser. No. 920,374, filed as PCT/EP92/00199, Jan. 30, 1992, abandoned.

[30] Foreign Application Priority Data

Jan. 30, 1991 [DE] Fed. Rep. of Germany ....... 4102741
Mar. 22, 1991 [DE] Fed. Rep. of Germany ....... 4109516

[51] Int. Cl.⁵ .......................................... G01N 27/26
[52] U.S. Cl. ..................................... 204/426; 204/424
[58] Field of Search ................ 204/424, 425, 426, 427

[56] References Cited

U.S. PATENT DOCUMENTS 4,283,261 8/1981 Maurer et al. ................. 204/426

Primary Examiner—Kathryn Gorgos
Assistant Examiner—Bruce F. Bell
Attorney, Agent, or Firm—Max Fogiel

[57] ABSTRACT

The invention concerns a device for continuously monitoring the level of at least one gaseous constituent in a mixture of gases. The drawbacks of the known devices are complexity, high power consumption, large size, and, due to their high mass, non-uniform distribution of temperature, entailing imprecise measurement, and inertia, especially at the commencement of operation. These drawbacks are eliminated with a base in the form of a water with at least two electrodes in the form of separated thin coatings and with a temperature sensor separated from the electrodes on one side and with a heater in the form of an electric-resistance heating coating on the other side.

13 Claims, 3 Drawing Sheets

DEVICE FOR MONITORING THE CONCENTRATION OF GASEOUS CONSTITUENTS IN MIXTURES OF GASES

The present application is a continuation of the parent application Ser. No. 920,374 filed as PCT/EP92/00199, Jan. 30, 1992, now abandoned.

BACKGROUND OF THE INVENTION

A device of this type is known (German OS 3 610 363). These known devices have on the whole proven practical.

They do have the drawback, however, of complexity. When the devices are manufactured in the form of probes, they must be gas tight and subjected subsequent to manufacture to a gas-tightness testing, increasing the prime cost of the probe. The probe cylinder must also accommodate a separate heater, which makes it larger and deteriorating the transfer of heat between the heater and the cylinder, entailing such additional drawbacks as high energy consumption and a non-uniform distribution of temperatures. Such a device occupies considerable space. Furthermore, the large masses take time to heat up, and the device cannot be operated until at least 60 seconds after it has been turned on. Again, relatively a lot of power is consumed in heating through the operation. Another essential drawback to the known system aside from its inertia is its only moderate precision, which results from the temperature sensitivity of the signals deriving from the sensor. Finally, a reference-gas mixture in the form of air must be supplied to the known device, meaning not only that the housing must be more complicated but that it cannot be installed anywhere desired.

Compensating for the temperature dependence of the known devices by incorporating a temperature sensor and computerized controls has already been conceived of. Such a device, however, is not yet known.

SUMMARY OF THE INVENTION

The object of the present invention is to improve the device by making it simpler, more suitable for detecting several gaseous constituents of a mixture, less bulky, capable of installation anywhere desired, more rapid in response, more accurate in results, and demanding less power for heat.

The base is a wafer with electrodes on one side and a preferably meandering resistance heating coating on the other. The heating coating heats the wafer up to operating temperature in a few seconds. A layer of an electrically insulating oxide can if necessary be interposed between the coating and the chip when voltages higher than those that destroy solid electrolytes (approximately 2 V for $ZrO_2$) are employed. The low mass and dimensions of the base wafer mean that only a little heat is necessary for continuous operation. If a sensor that measures the mean effective temperature in the immediate vicinity of the electrodes is mounted on one side, results will be as precise as possible. Using the wafer will also definitely reduce the installed mass without necessitating a complicated and expensive housing. Due to these slight dimensions and to the lack of the reference electrode that must be exposed to a reference gas (e.g. air) at the state of the art, the device in accordance with the invention can also be installed in difficult-to-reach places, in the exhaust section of a motor vehicle for example. Since the components are only coatings, the device is simple to manufacture by layering technique. No tightness testing is necessary. The device in accordance with the invention can also be employed to determine the levels of oxygen and its companions in the mixtures being measured.

The base in one advantageous embodiment of the invention is a ceramic wafer coated with a solid electrolyte. Little of this recalcitrant and expensive material—$ZrO_2$ doped with yttrium for example—is needed. Ceramic wafers again are mass-produced and inexpensive and exhibit the mechanical stability and insulation properties necessary to withstand the attachment of electric leads from the electrodes etc. Not just one but several electrodes are mounted on one side, each interacting with a specific constituent of the gas mixture. Such different constituents as CO, NO, or HC can be simultaneously detected along with $O_2$ with only a single housing, wafer, temperature sensor, and heating layer.

When the level of oxygen is constant, the signals will be between one electrode, acting as a reference, and each of the other electrodes. When on the other hand the level of oxygen in the mixture being monitored fluctuates, two of the possible electrochemical half cells are designed to measure the oxygen. One half cell is designed to advantage as a reference for solids (e.g. palladium or palladium oxide) and the other for determining the actual level of oxygen in the exhaust.

BRIEF DESCRIPTION OF THE DRAWINGS

One preferred embodiment of the invention will now be described by way of example with reference to the drawing, wherein.

DESCRIPTION OF THE PREFERRED EMBODIMENTS

Figure 1:
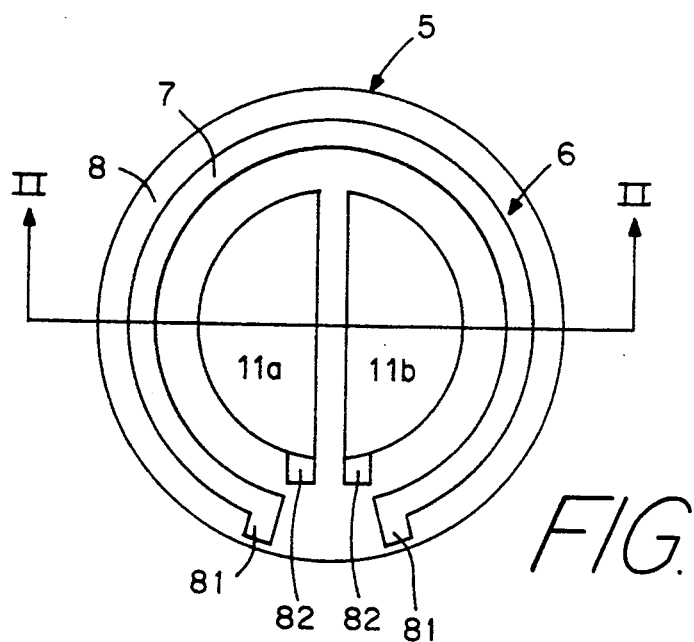
FIG. 1 is a top view of an embodiment with two electrodes that detect one constituent of a gas.

A device 5 has an electrochemical-cell base in the form of a wafer 6 of $ZrO_2$ with electrodes applied to one side 7 (FIG. 1). The electrochemical cells on side 7 are surrounded by a more or less round temperature sensor 8 with leads 81. The cells have leads 82. To these leads are connected unillustrated lines that extend to a processor.

Figure 3:
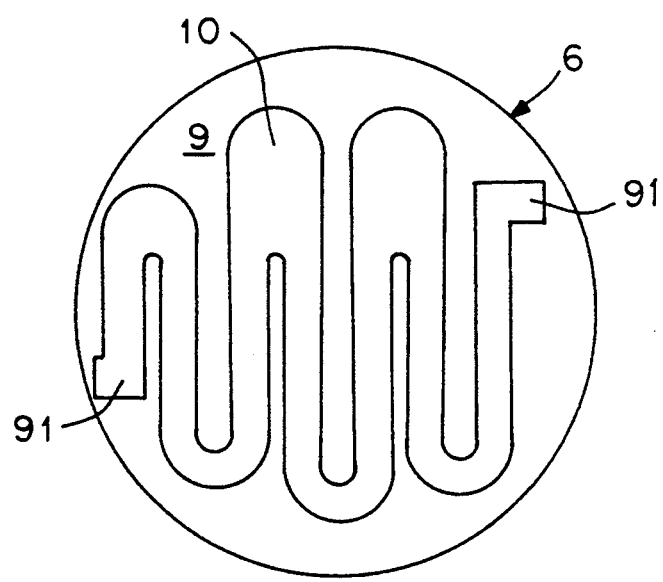
FIG. 3 is a bottom view of the embodiment illustrated in FIG. 1.

Meandering over the other side 9 of wafer 6 (FIG. 3) is a resistance-heating coating 10 with leads 91.

Figure 2A:
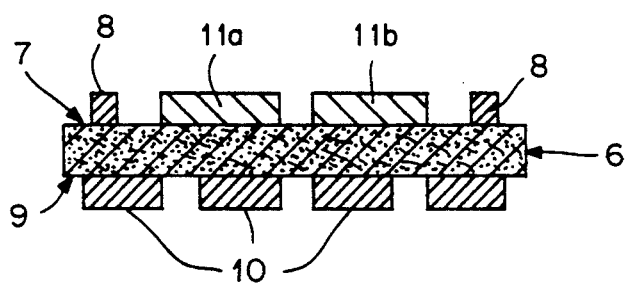
FIG. 2a is a section along the line II—II in FIG. 1.
Figure 2B:
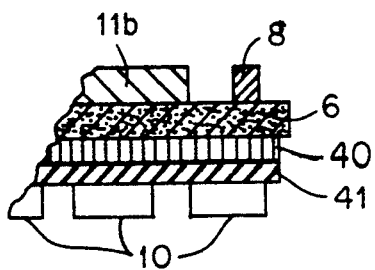
FIG. 2b is a partly truncated section through an alternative embodiment.

Also on side 7 of the thin wafer 6, which is round as viewed from above, are as will be evident from FIG. 2a two different electrodes 11a and 11b in the form of separated thin coatings that contain a metal or metal oxide. The overall device, which is manufactured by screen printing followed by sintering in a planar or thick-layer technology, is extremely slight in mass, takes up little space, and requires only a simple housing to accommodate it. Another advantage is that the mean effective temperature is determined directly in the immediate vicinity of the electrodes by means of the temperature sensor. The heating element is applied to the other side of the wafer, leaving little space between the resistance-heating coating and the electrodes and ensuring a short response time. Only a slight mass—the wafer and the separate layers on it—needs to be heated, so that operation consumes very little heat. A countervailing electrode 40 with a layer 41 of insulation under it that supports resistance-heating coating 10 is mounted on the underside 9 of the wafer 6 in the alternative illustrated in FIG. 2b to the embodiment illustrated in FIG. 2a. The test cell in this embodiment has even better timing.

Figure 4:
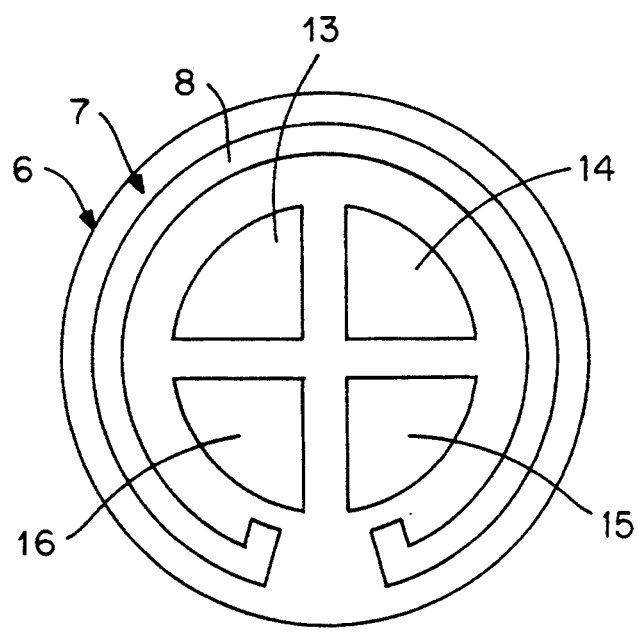
FIG. 4 is a schematic top view of another embodiment of the invention that simultaneously detects several constituent of a gas mixture.

It is of particular advantage for two or more different electrodes 13, 14, and 15 to be mounted on side 7 of wafer 6 as in the practical embodiment illustrated in FIG. 4. The electrodes simultaneously detect various constituents of the gaseous mixture. Another electrode 16 supplies a reference potential for the potentials of electrodes 13, 14, and 15.

Figure 5:
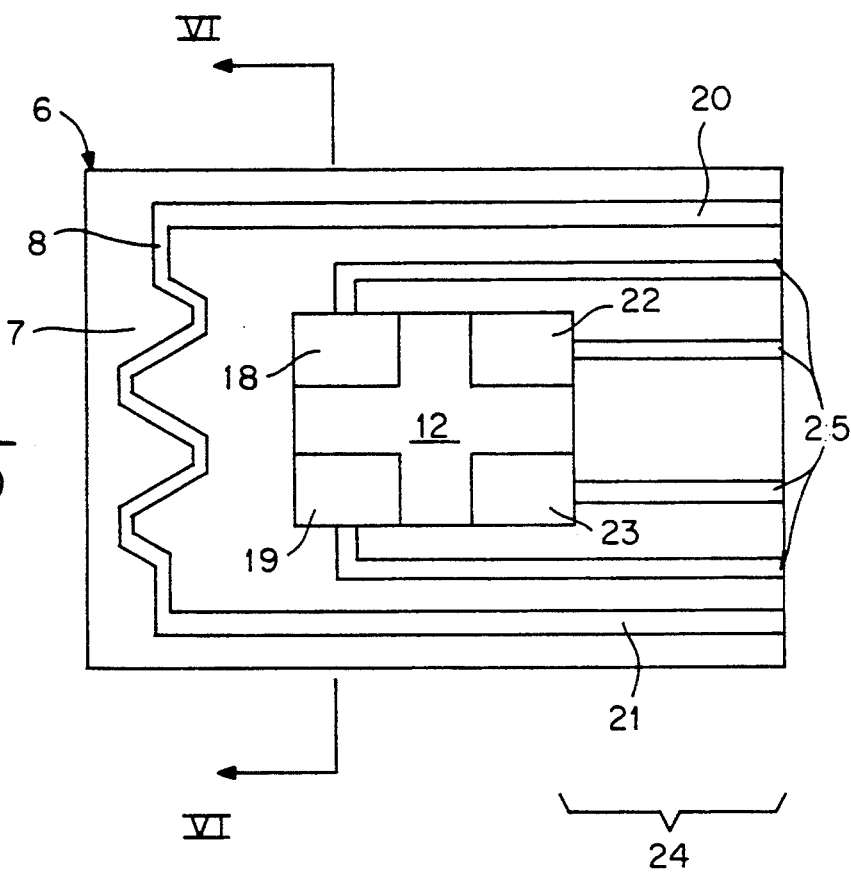
FIG. 5 is a schematic top view of a third embodiment of the invention.
Figure 6:
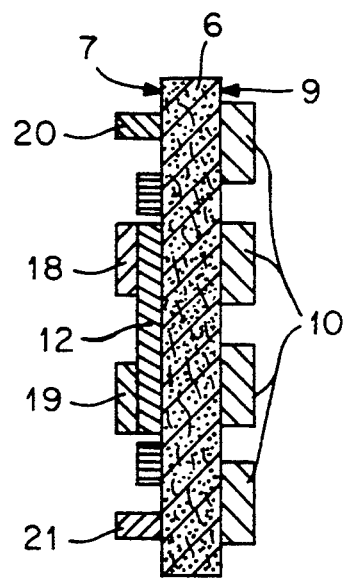
FIG. 6 is a section along the line VI—VI in FIG. 5.

FIG. 5 illustrates a third embodiment. A thin layer of a solid electrolyte 12, $ZrO_2$ stabilized with yttrium for example, is applied by the thick-layer technique to a wafer 6 of ceramic, preferably $Al_2O_3$. Also on side 7 of wafer 6 is a temperature sensor 8 and on the other side (FIG. 6) a resistance-heating coating 10. Mounted on the thin layer of the solid electrolyte 12 applied by the thick-layer technique are metal and/or metal-oxide electrodes 18, 19, 22, and 23 that selectively interact with other constituents of the mixture, allowing their concentration in the mixture being monitored to be determined.

To intercept the potentials of electrodes 18, 19, 22, and 23 and the signals from temperature sensor 8 and to supply a heating current to resistance-heating coating 10, electric connections in the form of strips of metal 20, 21, 25 are applied to the terminal area 24 of wafer 6. Terminal 24 makes it possible to connect the probe to lines far enough away from the test point. In summary, applicant provides an arrangement for continuously monitoring concentration of at least one gaseous constituent in mixtures of gases containing different constituents simultaneously as CO, NO or HC and $O_2$, in which a base is wafer-shaped and has at least two electro-chemical half cells with a solid electrolyte conducting oxygen ions in the base. A thin layer electrode is provided on the base with a solid porous structure that contains a metal and interacts with the gaseous constituent for generating a test signal that depends on the concentration of the constituents. A heater with electrical lines provides communications and intercept signals for processing electronically in a computer and converting into amounts of concentration. At least two electrodes are mounted on a first side of a wafer in the form of separated coatings. A temperature sensor is mounted on that same first side and is spaced from the electrodes. The heater has a resistance-heating coating that is mounted on a second side of the wafer.

According to the present invention, furthermore, the wafer is a solid electrolyte, and the test signals are conducted between each of the electrodes and the temperature sensor or the resistance-heating coating.

The temperature sensor extends around the electrodes and along an edge of the wafer. The temperature sensor meanders through the center region of the wafer. The wafer, furthermore, is of ceramic material that does not conduct ions, and the temperature sensor, the solid electrolyte, and the electrodes are mounted on one side of the wafer. The solid electrolyte may be in the form of a coating.

The wafer, moreover, has aluminum oxide and a terminal area bearing electrical lines. The solid electrolyte, moreover, may have stabilized zirconium diode.

The resistance-coating may be in the form of a meandering strip, and all coatings may be thick layer coatings. On the other hand, all the coatings may be screen-printed, and the electrodes may have gold.

We claim:

1. An arrangement for continuously monitoring concentration of at least one gaseous constituent in mixtures of gases containing different constituents simultaneously as CO, NO or HC and $O_2$, comprising: a base having a wafer shape; at least two electrochemical half cells with a solid electrolyte conducting oxygen ions in said base; each of said electrochemical half cells comprising an electrode in form of a thin layer on said base and having a solid porous structure containing a metal and interacting with said gaseous constituent for generating a test signal dependent on the concentration of said constituents; heating means with electrical lines for providing communications and intercept signals for processing electronically in a computer and converting into amounts of concentration, said wafer having a first side and a second side; at least two electrodes mounted on said first side of said wafer and comprising thin separated coatings; temperature sensing means mounted on said first side and spaced from said electrodes; said heating means having a resistance-heating coating mounted on said second side of said wafer; said wafer being a ceramic solid electrolyte; a counter electrode on said second side of said wafer; an insulating layer under said counter electrode and supporting said resistance-heating coating.

2. An arrangement as defined in claim 1, wherein said wafer is a solid electrolyte; and means for conducting said test signal between each of said electrodes and said temperature sensing means.

3. An arrangement as defined in claim 1, wherein said wafer is a solid electrolyte; and means for conducting said test signal between each of said electrodes and said resistance-heating coating.

4. An arrangement as defined in claim 1, wherein said temperature sensing means extends around said electrodes and along an edge of said wafer.

5. An arrangement as defined in claim 1, wherein said wafer has a center region between said electrodes, said temperature sensing means meandering through said center region.

6. An arrangement as defined in claim 5, wherein said wafer is of ceramic material; and a terminal connected to said electrical lines.

7. An arrangement as defined in claim 1, wherein said wafer is of ceramic material that does not conduct ions, said temperature sensing means, said solid electrolyte and said electrodes being mounted on said first side of said wafer, said solid electrolyte being a coating.

8. An arrangement as defined in claim 7, wherein said wafer comprises aluminum oxide.

9. An arrangement as defined in claim 1, wherein said solid electrolyte comprises stabilized zirconium dioxide.

10. An arrangement as defined in claim 1, wherein said resistance-heating coating is a meandering strip.

11. An arrangement as defined in claim 1, wherein all said coatings are thick layer coatings.

12. An arrangement as defined in claim 11, wherein all said coatings are screen-printed coatings.

13. An arrangement as defined in claim 1, wherein said electrodes have gold.

* * * * *